United States Patent [19]

Fulmer

[11] Patent Number: 4,832,796
[45] Date of Patent: May 23, 1989

[54] PROCESS FOR PURIFYING PHENOL

[75] Inventor: John W. Fulmer, Mt. Vernon, Ind.

[73] Assignee: General Electric Company, Mt. Vernon, Ind.

[21] Appl. No.: 74,214

[22] Filed: Jul. 16, 1987

[51] Int. Cl.$^4$ .............................................. B01D 3/34
[52] U.S. Cl. ...................................... 203/29; 203/95; 203/DIG. 6; 568/754
[58] Field of Search ................... 203/14, 96, 29, 95, 203/DIG. 6; 568/754, 753

[56] References Cited

U.S. PATENT DOCUMENTS

| | | | |
|---|---|---|---|
| 2,992,169 | 7/1961 | Gregory et al. | 568/754 |
| 3,029,294 | 4/1962 | Keeble | 203/29 |
| 3,265,594 | 8/1966 | De Jean et al. | 203/96 |
| 3,454,653 | 7/1969 | Larson | 568/754 |
| 3,692,845 | 9/1972 | Cheema et al. | 568/754 |
| 3,896,006 | 7/1975 | Cooke | 568/754 |
| 4,251,325 | 2/1981 | Marsh et al. | 568/754 |
| 4,328,377 | 5/1982 | Mori et al. | 568/754 |
| 4,351,967 | 9/1982 | Nishimura et al. | 568/754 |
| 4,504,364 | 3/1985 | Chen et al. | 203/96 |
| 4,567,304 | 1/1986 | Fulmer | 568/385 |

FOREIGN PATENT DOCUMENTS

| | | | |
|---|---|---|---|
| 0252394 | 6/1964 | Australia | 568/754 |
| 0621040 | 5/1961 | Canada | 568/754 |
| 0873604 | 7/1961 | United Kingdom | 203/29 |
| 1021759 | 3/1966 | United Kingdom | 568/754 |
| 01108584 | 4/1968 | United Kingdom | |
| 1231991 | 5/1971 | United Kingdom | 568/754 |
| 1394454 | 5/1975 | United Kingdom | 568/754 |

Primary Examiner—David L. Lacey
Assistant Examiner—V. Manoharan
Attorney, Agent, or Firm—Martin B. Barancik

[57] ABSTRACT

A process for improving the quality of phenol which comprises
(a) introducing a liquid phenol composition comprising above about 95 weight percent phenol on a dry basis, organic acid contaminants, and organic ketone contaminants;
(b) introducing water into the distillation tower, together with the phenol stream or in a separate stream;
(c) heating the phenol composition and water to a temperature sufficiently high to vaporize the water;
(d) allowing the organic acid contaminant to build to a concentration whereby sufficient acid is present to catalyze a reaction between an organic ketone contaminant and phenol, thereby forming a new compound(s) and;
(e) removing the said formed compound(s) from the distillation tower by hydroextractive steam distillation.

5 Claims, 1 Drawing Sheet

PROCESS FOR PURIFYING PHENOL

BACKGROUND OF THE INVENTION

Phenol and acetone have been mutually prepared by the cumene basic process for almost forty (40) years as disclosed in U.S. Pat. No. 4,567,304, hereinafter incorporated by reference. Cumene is peroxidized to give cumene hydroperoxide which is then acid cleaved to provide phenol and acetone. The phenol and acetone are then split by a distillation column via their separate boiling points followed by various purification procedures for both the phenol and acetone. Obviously by-products are formed as well as the desired products of phenol and acetone. Particularly detrimental to phenol quality are color embodying impurities generally of the carbonyl family. Of particular concern are the alpha-hydroxycarbonyls as typified by the main contaminant, alpha-hydroxyacetone. These particular compounds are deleterious to the quality of phenol, particularly in the coloring of end products from phenol. One of the quality tests utilized is the sulfonation color test wherein very small amounts of alpha-hydroxyacetone can provide very poor product implications to phenol. It is therefore very important to remove as much of these carbonyl contaminants from the phenol stream as possible.

This problem has been well recognized in the past as shown by a number of issued patents which have attempted to remove the carbonyl contaminants by expensive and elaborate processes. For example, Great Britain 1,108,584 removes the carbonyl contaminants from the phenol by contacting the carbonyl compound-contaminated phenol composition with a cation exchange resin such as the sulfuric, sulfonic, phosphoric and phosphonic substituted polystyrene cation exchange resins obtainable from Rohm and Haas. These resins catalyze a reaction involving the carbonyl compounds and converting them to materials which are lower boiling than phenol and thereby separatable from the phenol in a common distillation column. Great Britain No. 1,381,398 also separates the carbonyl impurities from the phenol composition wherein the phenol is substantially anhydrous by contacting the mixture with a solid acidic ion exchange resin insoluble in the mixture which converts the carbonyl containing impurities to products having boiling points higher than the boiling point of said phenol and distilling the phenol therefrom. Almost thirty years ago U.S. Pat. No. 3,029,294, hereinafter incorporated by reference, was applied for before the United States Patent Office. This patent removed the carbonyl contaminants from the phenol stream by contacting the carbonyl compounds with general catalyst including mineral acids, strong organic acids and solid surface active catalysts in order to convert the carbonyl compounds to substituted benzofurans by recondensing phenol with the carbonyl compounds and thereafter hydroextractively removing the benzofuran from the phenol as an overhead fraction. The organic acid is exemplified in U.S. Pat. No. 3,029,294 at column 2, lines 34-35 as a strong organic acid such as paratoluene sulfonic acid. It should be noted that all of these purification procedures start with a partially purified phenol made from the oxidation of cumene to the cumene hydroperoxide and then splitting the cumene hydroperoxide to phenol and acetone by a sulfuric acid catalyst system. These purification procedures disclosed and exemplified in the prior art references all use a new material not native to the general purification distillation procedures such as an ion exchange column or catalytically active materials such as alumina, mineral acids and montmorillonites, for example. Clearly such procedures are capital intensive and expensive operationally and can introduce further points for impurity contamination of the phenol and are outside the general utilized procedure.

It has now been discovered that these extraneous and expensive procedures for preparing a phenol purified from carbonyl contaminants are not necessary. Rather there is present in the phenol stream obtained from the initial distillation separation of acetone from phenol, native impurities, which if allowed to build to a critical concentration, can bring about a reaction between the carbonyl contaminant and phenol which thereby produces a compound which can readily be removed from the phenol by a procedure which is normally carried out in the recovery or in the purification procedures for phenol.

Current art-recognized phenol technology purifies the phenol fraction separated from the acetone fraction by a series of distillation towers. One of the towers is normally a "polishing" step for the phenol. Certain hydrocarbon or oil type materials are impurities carried along with the phenol stream. These hydrocarbon oil type impurities are removed from the phenol by a hydroextractive process. Introduced into a distillation tower is water to carry off the impurities from the phenol by an azeotroping or stream distillation technique. Also present in the column at this time are certain organic acid impurities. Up until this time these acid impurities are drawn off from the tower by side draws so as to not build up in concentrations since such organic acids would be corrosive to the ordinary tower material, stainless steel, at higher concentration.

We have surprisingly found that if these organic acid contaminants are allowed to build up in concentration, they reach a point where they catalyze a reaction between the carbonyl contaminants and the phenol thereby producing a compound which is readily removed by the hydroextractive steam distillation process already proceeding in the tower. The concentration of organic acids to the point which is catalytically active is also corrosive to the tower material. Such a build up of organic acids to the corrosive level is contrary to the teachings of the prior art. However, the production of the readily removable organic compound by hydroextraction techniques is clearly beneficial to the procedure since no extraneous materials need be added nor the phenol stream sidetracked to a specific ion exchange resin or any other technique for purging the phenol of the carbonyl contaminants. The reagents which catalyze the reaction are normally present in the phenol stream. Instead of removing them prior to the time they can catalyze the reaction, our invention allows them to build up to catalytic quantities. This concept had never been appreciated nor recognized in the prior art. This new process provides a low cost, highly efficient method for the further purification of phenol.

SUMMARY OF THE INVENTION

In accordance with the invention there is a process for purifying phenol:
  a. introducing into a distillation tower a liquid phenol composition comprising above about 95 weight percent phenol on a dry basis, organic acid contaminants, and organic carbon contaminants;
b. introducing water into the distillation tower together with the phenol stream or separate from the phenol stream or separate from the phenol stream;
c. heating the phenol composition and water to a temperature sufficiently high to vaporize the water;
d. allowing the organic acid contaminants to build to a concentration sufficiently high to catalyze a reaction between the organic carbonyl contaminants and the phenol, thereby forming a compound which is volatile in steam;
e. removing the said formed compound from the distillation tower by hydroextractive steam distillation.

DETAILED DESCRIPTION OF THE INVENTION

Phenol and acetone have been prepared from the oxidation of cumene industrially for a long period of time. The basic process involves oxidizing cumene to its hydroperoxide and then splitting the cumene hydroperoxide to acetone and phenol. The phenol and acetone are then purified in separate distillation trains and utilized commercially. One of the significant factors involved in phenol application is its carbonyl content. Various tests have been utilized for measuring the carbonyls in phenols. Among these is the sulfonation tests which involves the contacting of the phenol with concentrated sulfuric acid. The amount of color produced by such a reaction is a measurement of carbonyl impurities and the phenol purity. If the color is high, the phenol is impure. If the color is low or substantially no color appears, the phenol quality is considered to be high and can be utilized in various applications wherein a phenol having a high sulfonation color cannot be employed. The color is produced by a reaction between organic carbonyl impurities present in the phenol and concentrated sulfuric acid. Alpha-hydroxyacetone is the most prevalent of these organic carbonyl impurities and accounts for a significant amount of the color. Although it is not wished to be bound by this particular theory, it is believed that the alpha-hydroxyacetone is formed by oxidation of acetone by cumene hydroperoxide during the step of splitting the cumene hydroperoxide to phenol and acetone. Alpha-hydroxyacetone is known to be soluble in water and therefore very difficult to remove from phenol by a hydroextractive process. However, if the alpha-hydroxyacetone or other alpha-hydroxy carbonyl impurities can be made to react with the phenol, a benzofuran type molecule is prepared which is very susceptible to removal by hydro-extractive processes, i.e. steam distillation.

A further contaminant which is present in the phenol stream because of the processing techniques is organic acids such as, for example, carboxylic acids such as formic acid acetic and sulfur containing organic acids. One of the significant organic acids which is known to be present in acetic acid. Although not wishing to be bound by this pathway, it is believed that the acetic acid appears as a contaminant because the raw material cumene present initially is somewhat impure and contains small quantities of ethylbenzene. Cumene is made by the alkylation of benzene with propylene. Propylene is generally obtained by distillation of petroleum. Along with the propylene in the propylene cut from the distillation column must be some ethylene. The ethylene also alkylates the benzene thereby providing ethylbenzene, which contaminates the cumene. The ethylbenzene is oxidized to its peroxide compound during the oxidation process. During the splitting process the ethylbenzene peroxide is split to phenol and acetaldehyde. Through various reaction conditions present in the normal pathways in the phenol acetone process, the acetaldehyde is oxidized to acetic acid. This pathway is outlined below.

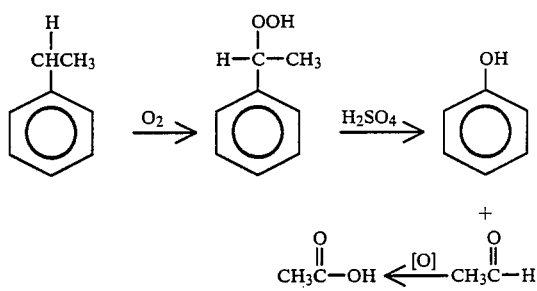

The organic acid contaminants and organic carbonyl contaminants flow through the phenol purification scheme and are present in the distillation tower in the phenol purification train wherein a hydroextractive distillation occurs. In one embodiment of the process a phenol stream carrying the organic acid and organic carbonyl contaminants are introduced into a distillation tower together with a stream of water. The phenol stream is usually obtained from a prior distillation tower wherein the phenol stream is separated as overhead from the heavy ends. The water can be introduced separately from the phenol stream or may be added specifically to the phenol stream prior to introduction into the distillation tower. The water is employed so that under the temperature present in the distillation tower the hydroextraction process occurs wherein contaminant oils present in the phenol stream are removed from the phenol as an azeotrope. Examples of such "oils" include 2-methylbenzofuran, alphamethylstyrene, 2-phenyl-butene and $C_6$–$C_9$ ketones, such as 3-methylcyclopentenone. Although some of these "oils" may have boiling points significantly different than phenol, they have an affinity and a tendency to group together with phenol in the distillation towers. Generally also present in the tower, although not necessarily desired, is a water/phenol azeotrope which is also removed. As previously stated, the carbonyl contaminants are soluble in the water and are therefore not removed to a great extent by the hydroextractive distillation. Rather these carbonyl contaminants make their way further down the tower into the higher temperature regions. Also present in these higher temperature regions are grouped the acid contaminants where they are collected in the dynamic equilibrium occurring on the plates of the column. The general instructions for operating this purification column in the phenol industry is that a side draw be employed at the plates wherein the organic acids tend to accumulate. The organic acid contaminants are drawn off periodically so as to not allow the organic acid contaminants to build up to an acidic concentration which would be corrosive to the column.

We have now discovered that in so doing, the organic acids are not allowed to build up to a concentration where they can be effective to catalyze the reaction between the carbonyl contaminants, specifically alpha-hydroxyacetone, and the phenol to produce a new compound which can be readily hydroextracted. Because of the increased concentration of organic acid, it is preferred and desirable to use a corrosion resistant alloy at the tower section wherein the organic acid contaminants are allowed to build up in concentration. Without such an acid corrosion resistant alloy, the usual types of materials used in a column, such as stainless steel, would become damaged. The acids are still preferably withdrawn by the side draws but at a much higher concentration than the general teachings. The quality of the phenol prepared in the manner of this invention and as measured by the sulfonation test is very high. In fact the phenol appearing at the bottom of the tower generally has no measurable alpha-hydroxyacetone concentration.

By proceeding contrary to the teachings of the recognized art in phenol processing, it has now been shown that ordinary acid contaminants known to be native to the process streams can be employed to catalyze a reaction which removes one of the most difficultly removable impurities from the phenol stream. Unusually pure phenol as measured by the sulfonation test is obtained by a process which is low in capital and operating cost.

BRIEF DESCRIPTION OF THE DRAWING

The invention will be further discussed with respect to FIG. 1 which shows a distillation tower which is a specific embodiment of the general invention.

With respect to FIG. 1, the process includes the distillation tower 10 in which the impure phenol feed stream 12 is introduced near the top of the tower. The phenol stream is at least 95 weight percent phenol, preferably above about 97 weight percent phenol, and more preferably above 98 weight percent phenol. The calculation of the phenol weight is on the dry basis. Also present in the phenol stream are carbonyl contaminants and organic acid contaminants. The phenol stream entering the distillation tower at this point is frequently the overhead of a previous distillation tower which separates phenol and its companion materials from higher boiling materials. Water may be introduced into the distillation tower 10 together with the phenol stream or apart from the phenol stream as in line 14. The water source enters from line 8, the phenol stream, 12, and water enter the distillation tower and the phenol stream is held generally at a temperature of from about 180° to about 210° F., generally from about 195° to about 205° F. At the bottom of the distillation tower, line 22 brings off anhydrous liquid purified phenol at a temperature of from about 400° to about 420° F. and moderate pressure. Line 24 takes an amount of the liquid phenol and recycles it to the column after going through a reboiler, 28 which is heated with steam. It is this heated phenol which provides the increased temperature in the distillation tower and brings about azeotropes and continuous boiling and liquification of the substances on the various internal plates of the distillation tower so that fractional separations may occur. The phenol feed works its way down the distillation tower wherein it is undergoing an azeotrope with the water present, the azeotrope constantly being drawn off overhead by line 18. Together with the water-phenol azeotrope there is also a water contaminant oil azeotrope also being drawn off which further purifies the phenol. However, some of the carbonyl contaminants do not easily azeotrope off with water and thereby would go down the column with the phenol and be brought out of the column at line 22 under ordinary circumstances. Generally, the carbonyl contaminants are of a relatively small concentration, however they do produce a significant change in the sulfonation color test. Contamination with alpha-hydroxyacetone in phenol product can vary from about 10 to about 100 parts per million in general. As the temperature of the column grows higher in its downward phenol progression, most of the water and phenol azeotrope and water and oil azeotropes that are readily drawn off as overhead has occurred to about two-thirds of the column length as measured from the top. At this point, the organic acid contaminants start building up due to their boiling points. The specific means of operating the column as presently operated in the art is to draw off the organic acid contaminants by the side draws shown, 16, so as to avoid an organic acid buildup which would be highly corrosive to the distillation tower materials. The process of this invention differs in that the acid concentration is allowed to buildup until it reaches a level that catalyzes the reaction between the carbonyl contaminants, particularly alpha-hydroxyacetone and the phenol, thereby producing a compound which is readily volatilizable with water in an azeotropic fashion and leaves at the top of the column via line 18 together with the water/oil azeotrope and water/phenol azeotrope. Line 18 goes to drum 20 wherein the phenol and water is separated from the carbonyl contaminant phenol reaction product and the other extracted oil contaminants and the phenol and water recycled to the distillation tower in line 14. The extracted oil contaminants are removed from drum 20 by line 36. Although it is not positive that this particular compound is formed, as is shown below it is known that alpha-hydroxyacetone will react with phenol under acidic conditions to produce 2-methylbenzofuran which is readily volatilizable in a hydroextractive process as being practiced in this column.

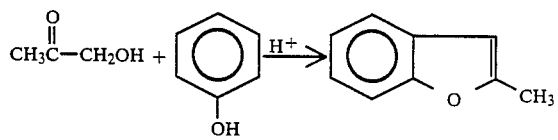

Figure 1:
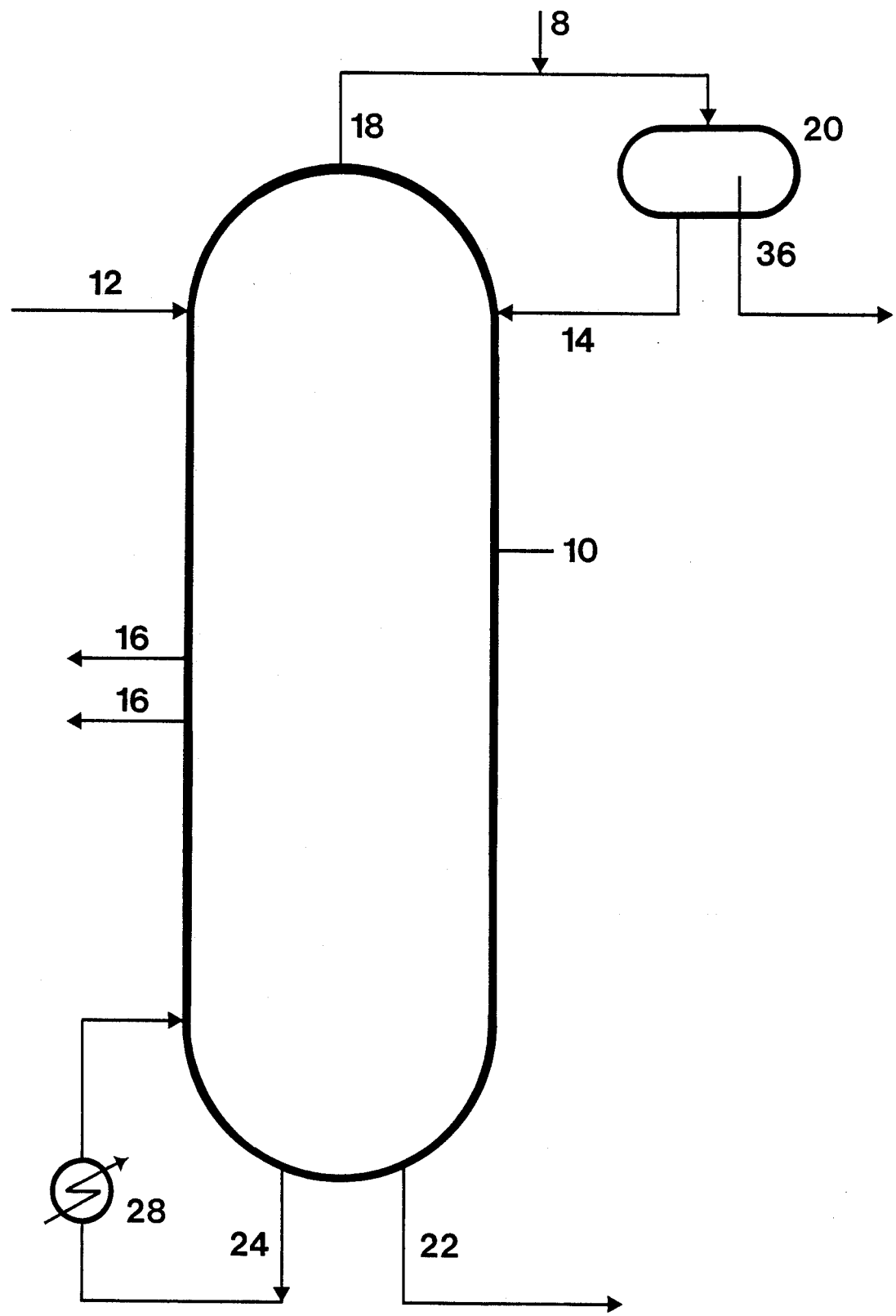

Below are specific comparative examples showing the removal of the carbonyl contaminants by the old process and the removal of the carbonyl contaminants by the new process. It should be noted that the general acid level which can acceptably catalyze the reaction is below a pH of about 2.5, preferably below a pH of about 2.0.

In the results presented below the laboratory sulfonation test was run as normally done in the art, mixing concentrated sulfuric acid with a portion of the phenol stream, allowing the color to develop and measuring the color. The higher the color present, the lower is the percent light transmission. Values above 90% transmission are considered to be indicative of exceptionally high quality phenol, which is very difficult and expensive to produce by the prior methods. There is a considerable difference in phenol purity in sulfonation test percent transmission scores above 90% and below 90%. Also present in the data tabulated below are parts per million (ppm) values for the alpha-hydroxyacetone (HA) present in the phenol. Both the sulfonation tests and HA tests were taken on a plant phenol distillation tower bottom, the distillation tower operating in essentially the same manner as shown in FIG. 1. The phenol effluent produced by the prior art low organic acid level method was sampled every day for both sulfonation test percent transmission and HA values for a period of 31 days and then for an additional 31 days the phenol effluent produced by the invention higher organic acid level was also analyzed for sulfonation test percent transmission and HA values. The values presented below are the arithmetic average of the 31 days for each test system.

TABLE I

|  | PRIOR ART LOW ACID LEVEL | INVENTION HIGH ACID LEVEL |
|---|---|---|
| SAD % T | 89.8 | 92.3 |
| HA PPM | 14.0 | 0.2 |

As can be observed by the above data, the alpha-hydroxyacetone levels have been reduced more than 98% merely by allowing a "contaminant" to reach an appropriate concentration. Outstanding quality of phenol as measured by the SAD transmissions value is also obtained at essentially no increase in operating cost or capital investment.

What is claimed is:

1. A process for improving the quality of phenol which comprises
   (a) introducing into a distillation tower a liquid phenol composition comprising above about 95 weight percent phenol on a dry basis, organic acid contaminants, and organic ketone contaminants;
   (b) introducing water into the distillation tower, together with the phenol stream or in a separate stream;
   (c) heating the phenol composition and water to a temperature sufficiently high to vaporize the water;
   (d) allowing the organic acid contaminant to build to a pH of less than about 2,5, whereby sufficient acid is present to catalyze a reaction between an organic ketone contaminant and phenol, thereby forming a new compound(s) and;
   (e) removing the said formed compound(s) from the distillation tower by hydroextractive steam distillation.

2. The process in accordance with claim 1 wherein at least a portion of the organic ketone contaminant is alpha-hydroxyacetone.

3. The process in accordance with claim 1 wherein at least a portion of the organic acid contaminant is acetic acid.

4. The process in accordance with claim 2 wherein at least a portion of the organic acid contaminant is acetic acid and/or formic acid.

5. The process in accordance with claim 1 wherein the organic acid contaminant is allowed to build to a pH of less than about 2.0.

* * * * *

UNITED STATES PATENT AND TRADEMARK OFFICE
CERTIFICATE OF CORRECTION

PATENT NO. : 4,832,796

DATED : May 23, 1989

INVENTOR(S) : John William Fulmer

It is certified that error appears in the above-identified patent and that said Letters Patent is hereby corrected as shown below:

Column 3
Line 2
"carbon" should read "carbonyl"

Column 3
Line 5
After the 1st. "stream" add ";"

Column 3
Line 5
Delete "or separate from the phenol stream;"

Signed and Sealed this

Fourth Day of September, 1990

Attest:

HARRY F. MANBECK, JR.

*Attesting Officer*     *Commissioner of Patents and Trademarks*